Figure 1:
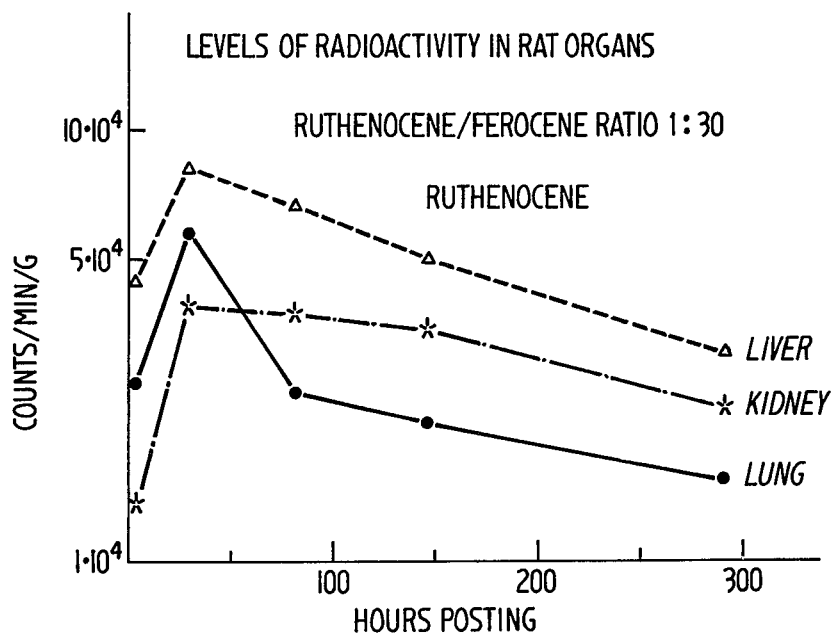

United States Patent [19]

Wenzel et al.

[11] 4,028,389

[45] June 7, 1977

[54] METALLOCENES AND METALLOCENE DERIVATIVES HAVING A RADIOACTIVE CENTRAL ATOM

[75] Inventors: Martin Wenzel; Detlef Langheim, both of Berlin, Germany

[73] Assignee: Schering Aktiengesellschaft, Berlin & Bergkamen, Germany

[22] Filed: Sept. 21, 1973

[21] Appl. No.: 399,552

[30] Foreign Application Priority Data

Sept. 21, 1972 Germany ............................ 2246460

[52] U.S. Cl. ................. 260/429 CY; 260/438.5 R; 260/439 CY; 424/1
[51] Int. Cl.$^2$ .................. C07F 17/02; C07F 17/00
[58] Field of Search ............. 260/429 CY, 439 CY

[56] References Cited

UNITED STATES PATENTS 3,045,119  7/1962  Haney et al. ................ 260/439 CY

FOREIGN PATENTS OR APPLICATIONS 706,905    3/1965  Canada
1,049,860  2/1959  Germany
1,057,114  5/1959  Germany
1,059,452  6/1959  Germany

OTHER PUBLICATIONS

Gauthier, J. Chem. Soc. D p. 690 (1969).
Chem. Abstracts vol. 68, 2978c (1968).
Cotton, Progress in Inorganic Chemistry, Interscience Publ. Inc. N. Y. p. 32 (1959).
Ekemark et al., Acta Chem. Scand. vol. 16, pp. 1136–1138 (1962).
Sutin et al., J. Inorg. Nucl. Chem. vol. 6, pp. 91 to 98 (1958).

*Primary Examiner*—Helen M. S. Sneed
*Attorney, Agent, or Firm*—Millen & White

[57] ABSTRACT

Radioactive metallocenes and metallocene derivatives are prepared by heating a non-radioactive metallocene or metallocene derivative with a radioactive metal salt, e.g., $Ru^{103}Cl_3$, at 140°–250° C.

14 Claims, 2 Drawing Figures

METALLOCENES AND METALLOCENE DERIVATIVES HAVING A RADIOACTIVE CENTRAL ATOM

BACKGROUND OF THE INVENTION

This invention relates to radioactive metallocenes and metallocene derivatives and to a process for the production thereof.

Non-radioactive metallocenes, i.e., metal derivatives of cyclopentadiene, and metallocene derivatives, i.e., metallocenes wherein at least one cyclopentadienyl radical bears a substituent are known. "Chemistry of the Iron Group Metallocenes," John Wiley and Sons, New York, London and Sidney (1965).

$Co^{60}$-cobaltocene, $Ru^{103}$-ruthenocene, $Ru^{103}$-monoacetyl rethenocene and $Fe^{59}$-ferrocene are also known in the prior art. See Fed. Rep. of Germany Patents 1,049,860 and 1,057,114; J. Inorg. Nuc. Chem. 6 (1958), 91. See also Gauthier, J. Chem. Soc. 1969, p. 690.

SUMMARY OF THE INVENTION

According to the process of this invention, A non-radioactive metallocene or metallocene derivative is heated with a radioactive metal in ionic form at 140°–250° C. for 0.1 – 200 hours.

DETAILED DISCUSSION

The process of this invention provides a simple method of synthesizing radioactive metallocenes and metallocene derivatives from the corresponding non-radioactive compounds.

By substituting the non-radioactive central atom in a metallocene by a radioactive nuclide, it is possible to incorporate suitable radioisotopes into modifiable organic molecules in a chemically and biologically stable manner.

By this process, approximately 10–70% of the radioactivity of the radioactive starting material is retained in the form of a radioactive metallocene or metallocene derivative.

In contrast to the process of Gauthier, supra, the heating process of this invention must not be effect at excessively high temperatures or excessively long reaction times because otherwise the thus-produced radioactive organometallic compounds are decomposed. Thus, the maximum reaction temperature and reaction time is dictated by the stability of the starting metallocene or metallocene derivative.

Although the reaction can be conducted at 140°–250° C., depending on the reactivity and stability of the selected metallocene, temperatures of 150°–200° C. and a reaction time of 0.1–3 hours are especially advantageous, with the optimum reaction time generally being inversely proportional to the reaction temperature. The reaction is conducted in the absence of an atmosphere, e.g., at a vacuum of $10^{-2}$ torr [mm. Hg], an inert gas is utilized, or both.

The starting metallocenes and metallocene derivatives are those wherein the metal is preferably Fe, i.e., ferrocenes. Other include Co, Ni, Cr, etc.

Both the simple, i.e., unsubstituted, non-radioactive metallocenes and the derivatives thereof can be employed as starting materials, e.g., wherein at least one cyclopentadienyl radical is substituted, e.g., by —COOH, —COO-alkyl, —CONH$_2$, 1–4 carbon atoms, alkyl containing 1–8, preferably 1–4 carbon atoms, halogen, amino or dialkylamino. The exact nature of the substituent on the cyclopentadienyl ring is not critical.

Ferrocene and its derivatives can be employed particularly advantageously as the inactive metallocene in the process of this invention. Radioactive metallocenes can be produced, for example, from the following inactive ferrocene derivatives:

|  | Radiochemical Yields |
|---|---|
| Ferrocene | 70% |
| Ferrocene monocarboxylic acid | 8% |
| Ferrocene monocarboxylic acid amide | 20.40% |
| Methyl ester of ferrocene monocarboxylic acid | 15% |
| Ferrocene monoacetyl | 15% |
| Ferrocene diacetyl | 30% |

It is, of course, also possible to employ other non-radioactive active ferrocene derivatives and metallocene derivatives for the process, including those described in the literature. See "Chemistry of the Iron Group Metallocenes," supra, the disclosure of which is incorporated by reference.

Suitable radioactive central atom starting materials are those capable of metallocene formation. Especially advantageous for this purpose are radioactive nuclides of the Group VIII metals of the periodic table, e.g., iron, cobalt, ruthenium and osmium. Examples of such radioactive nuclides are:

$Fe^{52}$, $Fe^{59}$, $Co^{58}$, $Ru^{95}$, $Ru^{103}$ and $Os^{193}$.

Radioactive nuclides from other groups of the periodic table can be utilized, for example nuclides of Subgroups VI and VII, such as $Cr^{51}$, $Mn^{54}$ or $Tc^{99m}$. The sole requirement is that they are capable of forming a metallocene.

The radioactive metal is conveniently employed as an ionic salt, e.g., chloride, nitrate, sulfate, or any other water soluble salt of a strong organic or an inorganic acid.

In the process of this invention, it is possible to select those radioactive nuclide ions which have nuclear-physical data suitable for purposes of nuclear medicine and scintigraphy. By selecting the specific activity of the radioactive metal ions, optionally even carrier-free, the specific activity of the radioactive metallocenes and/or metallocene derivatives can be regulated.

Since the process of this invention is a one-stage process, it is also possible to employ nuclides having a short half-life, e.g., nuclides separated from "isotope generators."

The radioactive compounds produced in accordance with the process of this invention can be utilized directed or after further chemical processing. For example, the thus-produced radioactive metallocenes or metallocene derivatives can be oxidized or reduced, depending on the oxidation stage of the central atom. Furthermore, it is possible, for example, to tag proteins with radioactive metallocene acid chlorides or metallocene isothiocyanates, or similarly reactive derivatives. These tagged proteins can be utilized in nuclear medicine.

Figure 2:
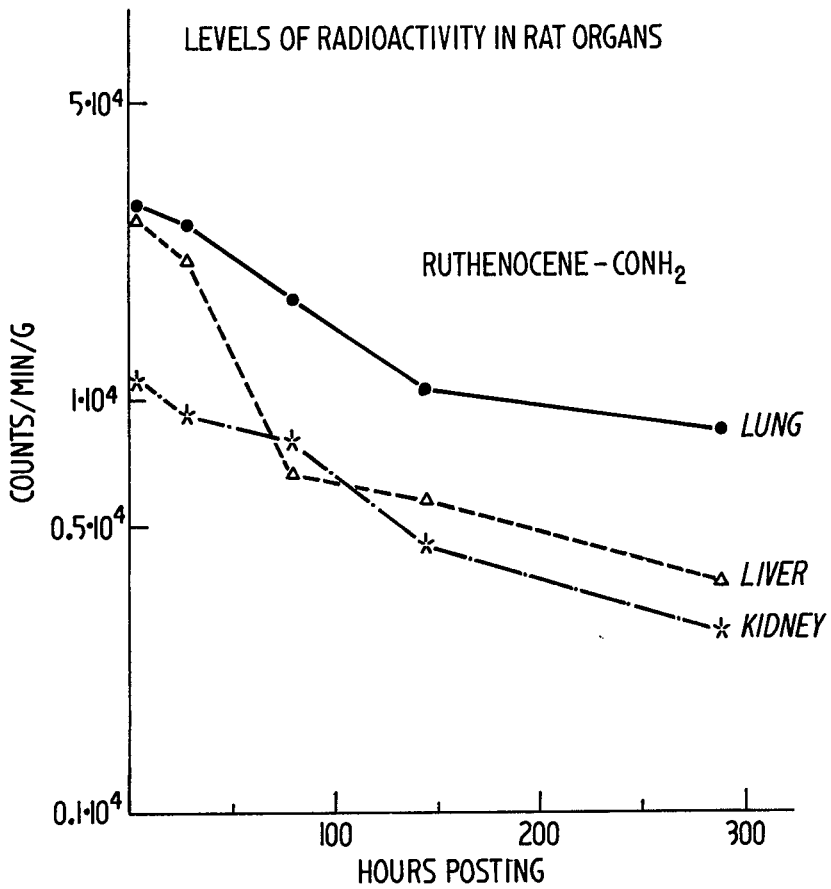

Since Metallocenes, e.g., $Ru^{103}$-ruthenocene monocarboxylic acid amide, are concentrated in the liver and lungs, scintigrams of these organs in nuclear-medical diagnostics can be produced employing these compounds. FIGS. 1 and 2 show the enrichment of $Ru^{103}$-ruthenocene and $Ru^{103}$-ruthenocene monocarboxylic acid amide, respectively, in the liver, kidneys and lungs of rats at various periods of time after intraperitoneal injection of Ca. 4μCi ($\cong$700 γ/kg.), measured in scintillations per minute per gram.

The radioactive reaction products are filled into ampoules in an aqueous-alcoholic solution or suspension and then sterilized, for use in nuclear medicine, preferably for scintigraphy. The solutions or suspensions are preferably administered intravenously in amounts of 0.1 – 5 ml. The concentration of the radioactive substance in the injection preparation ranges below 1 μmole/ml.

Furthermore, by employing lipophilic radioactive metallocene derivatives, it is possible to effect a radioactive labeling of petroleum products.

A primary advantage of this invention is that modifiable organic compounds are obtained in a simple manner, which compounds contain, bound in a stable condition, a radioactive metallic atom which, in turn, can be selected in correspondence with the requirements of the measuring technique of nuclear-medical diagnostics with respect to energy and half-life of their radiation.

Since the desired metallocene derivative is usually first prepared in non-radioactive form, it is thus unnecessary to conduct additional organic-preparative reactions with the radioactive metallocene, which greatly facilitates the handling of the radioactive compounds.

Radioactive Labeling

The labeling procedure generally comprises the following steps:
a. Preparation of a mixture of inactive metallocene and radioactive metallic ion.
b. Heat treatment of the reactants.
c. Working up of the reaction product.

A. Preparation of a Mixture of Inactive Metallocene and Radioactive Metallic Ion Any means of contacting the selected source of metallic ionic radioactivity with the selected metallocene can be employed, e.g., dissolving one in a solvent solution of the other or mixing the two solutions. Generally, it is preferred to employ solutions of both reactants. Preferred solvents are alcohols, e.g., ethanol; or ketones, e.g., acetone. After evaporation in vacuo an intimate mixture of the components is obtained.

Co-precipitation is a preferred method for achieving the metallocene-ion contact necessary for the exchange of metal ions. In the experiments below, an inert gas, e.g., nitrogen, was introduced into the reaction vessel in an ethanolic solution to remove atmospheric oxygen. The dimensions of the tempered quartz ampoule employed in the examples below were as follows: length, 6 cm.; internal diameter, 2 cm. Using a graduated disposable syringe, the desired amount of radioactivity in the form of ethanolic solution of the selected salt was added, the solvent was gently removed under vacuum at about $10^{-2}$ to $10^{-3}$ torr, and the ampoule was then sealed by melting at this pressure.

Purging with purified nitrogen resulted in a minor increase in yield.

B. Heat Treatment of the Reactants

The heating can be conducted over a temperature spectrum of 140°–250° C. for 0.1 – 200 hours. A temperature of 150°–200° C. and a heating time of 0.1–3 hours is preferred. A temperature of 180° C. and a heating period of 1–3 hours was employed in the examples below.

C. Working up the Reaction Product

In the final step of the process of this invention, the radioactive metallocene obtained by the heating step is separated from any residual starting radioactive ionic metallic starting material and preferably also the starting non-radioactive metallocene. This can be accomplished by any conventional procedure, e.g., fractional crystallization, but column chromatography is preferred.

In the examples below, the cooled-down ampoule was carefully opened and the contents thereof were removed by dissolving with a suitable organic solvent. A preliminary purification was effected over a column with $Al_2O_3$ (length, 20 cm.; internal diameter, 1.0 cm.). Further purification was effected by thin-layer chromatography.

Without further elaboration, it is believed that one skilled in the art can, using the preceding description, utilize the present invention to its fullest extent. The following preferred specific embodiments are, therefore, to be construed as merely illustrative and not limitative of the reminder of the disclosure in any way whatsoever.

EXAMPLE 1

$Ru^{103}$-Ruthenocene Monocarboxylic Acid Amide

A solution of 10 mg. of ferocene-$COHN_2$ in 0.5 ml. of ethanol is mixed with 1–4 mCi of a solution of $Ru^{103}Cl_3$ in 1.0 ml. of ethanol and after evaporation in vacuo the reaction vessel is sealed and heated for 1 hour at 180° C. Thereafter, the reaction mixture is extracted three times with one-ml. portions of acetone. the resulting solutions are introduced onto an column of alkaline $Al_2O_3$ (Woelm, activity stage II) and eluted therefrom with acetone. The first "acetone fraction" contains, inter alia, $Ru^{103}$-ruthenocene-$COHN_2$ which can be sublimed to an extent of about 30–40%. A mixture of predominantly ferrocene-$CONH_2$ and the desired $Ru^{103}$-ruthenocene-$CONH_2$ is obtained by subsequent elution with ethanol. Inorganic $Ru_{103\ 3}^+$ and other decomposition residues remain on the column. A very pure mixture of ferrocene- and ruthenocene-monocarboxylic acid amide is obtained in this manner. Further purification, if desired, can very easily be accomplished using silicagel plates (Merck F254, 0.25 mm.).

Eluent: benzene: ethanol (10.2).

The yield of radioactive $Ru^{103}$-ruthenocene-$CONH_2$, based on the starting radioactivity employed, is 22–25%.

EXAMPLE 2

$Ru^{103}$-Ruthenocene Monocarboxylic Acid Methyl Ester

By heating a mixture according to Example 1 of 50 mg. of the methyl ester of ferrocene monocarboxylic acid and of 1400 μCi of $Ru^{103}Cl_3$ (specific activity 126 μCi/μmol Ru) to 170° C. at $10^{-2}$ torr for a period of 3 hours, the iron of the ferrocene is partially exchanged for radioactive ruthenium, thus obtaining the corresponding ruthenocene derivative. The radioactive ruthenocene derivative can very easily be separated from other radioactive by-products by thin-layer chromatography, as demonstrated by a direct measurement on the chromatogram. In addition to the main product, there is obtained radioactive ruthenocene and inorganic starting material. The radiochemical yield is about 15% of the employed inorganic $Ru^{103}$ activity. The identity of the radioactive methyl ester of ruthenocene monocarboxylic acid eluted from the chromatogram at an $R_f$ value of 0.3 was proven by hydrolysis to ruthenocene monocarboxylic acid.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of metallocenes or metallocene derivatives with a radioactive central atom, which comprises heating at 150°–200° C. for 0.1–3 hours a non-radioactive metallocene or metallocene bearing a substituent selected from the group consisting of —COOH, —COO-alkyl, $CONH_2$, alkanoyl, halogen, amino or dialkylamino wherein alkyl and alkanoyl in each instance are of 1–8 carbon atoms on at least one cyclopentadienyl radical, with a radioactive metal nuclide selected from Group VIII and Subgroups VI and VII of the Periodic Table which is capable for forming a metallocene in ionic form and thereafter separating the thus-obtained radioactive metallocene or metallocene derivative from the ionic radioactive starting material.

2. A process according to claim 1 wherein at least one cyclopentadienyl radical of the starting metallocene is substituted by —COOH, —COO-alkyl, $COHN_2$, alkanoyl, halogen, amino or dialkylamino wherein alkyl and alkanoyl in each instance are of 1–8 carbon atoms.

3. A process according to claim 2 wherein the metallocene is a ferrocene.

4. A process according to claim 3 wherein the non-radioactive starting metallocene is selected from the group consisting of ferrocene, ferrocene monocarboxylic acid, ferrocene monocarboxylic acid amide, methyl ester of ferrocene monocarboxylic acid, ferrocene monoacetyl and ferrocene diacetyl.

5. A process according to claim 1 wherein the radioactive ionic starting material is a metal of Subgroup VIII of the periodic table.

6. A process according to claim 5 wherein the ionic radioactive starting material is ionic iron or ruthenium.

7. A process according to claim 6 wherein the radioactive ionic starting material is a water soluble iron or ruthenium salt of a strong acid.

8. A process according to claim 7 wherein the salt is a $Ru^{103}$ salt.

9. A process according to claim 8 wherein the salt is $Ru^{103}Cl_3$.

10. A process according to claim 7 wherein the non-radioactive starting metallocene is selected from the group consisting of ferrocene, ferrocene monocarboxylic acid, ferrocene monocarboxylic acid amide, methyl ester of ferrocene monocarboxylic acid, ferrocene monoacetyl and ferrocene diacetyl.

11. A process according to claim 10 wherein the salt is a $Ru^{103}$ salt.

12. $Ru^{103}$-Ruthenocene Monocarboxylic Acid Amide.

13. $Ru^{103}$-Ruthenocene-Monocarboxylic Acid Methyl Ester.

14. A process according to claim 1 wherein the starting non-radioactive metallocene is ferrocene monocarboxylic acid methyl ester or ferrocene monocarboxylic acid amide, the radioactive metal in ionic form is a $Ru^{103}$ salt of a strong acid and the reaction is conducted in the absence of solvent with the salt in intimate physical mixture with the starting metallocene.

* * * * *